United States Patent [19]

Imai et al.

[11] Patent Number: 4,698,449

[45] Date of Patent: Oct. 6, 1987

[54] CRYSTALLINE SILICATES, AND PROCESSES FOR THE PRODUCTION OR USE THEREOF

[75] Inventors: Tetsuya Imai; Hiroshi Fujita, both of Hiroshima; Minoru Koikeda; Takashi Suzuki, both of Yokohama, all of Japan

[73] Assignee: Research Association for Petroleum Alternatives Development, Tokyo, Japan

[21] Appl. No.: 891,337

[22] Filed: Jul. 31, 1986

Related U.S. Application Data

[60] Division of Ser. No. 736,988, May 23, 1985, which is a continuation of Ser. No. 491,534, May 4, 1983, abandoned.

[30] Foreign Application Priority Data

May 4, 1982 [JP] Japan ................................. 57-73453
May 4, 1982 [JP] Japan ................................. 57-73454
May 4, 1982 [JP] Japan ................................. 57-73455

[51] Int. Cl.$^4$ .............................................. C07C 1/04
[52] U.S. Cl. ............................. 585/469; 423/326; 423/331; 423/332; 502/73; 502/65; 502/263; 518/713; 518/717; 518/721; 585/640; 585/733; 585/408

[58] Field of Search ............... 585/469, 640, 733, 408; 502/74, 65, 73, 263; 423/326, 331, 332; 518/713, 714, 717, 721

[56] References Cited

U.S. PATENT DOCUMENTS 4,591,576  5/1986  Chiang et al. ......................... 502/65
4,622,308 11/1986  Koikeda et al. ...................... 423/329
4,634,686  1/1987  Desmond et al. ................... 423/326

FOREIGN PATENT DOCUMENTS 7012093  1/1982  Japan ................................. 585/469

*Primary Examiner*—Asok Pal
*Attorney, Agent, or Firm*—Wenderoth, Lind & Ponack

[57] ABSTRACT

This invention relates to a novel crystalline silicate useful as a catalyst for various organic reactions such as polymerization of organic compounds, alkylation, isomerization, disproportionation and the like, which has a chemical composition represented by the general formula in the terms of mole ratios of oxides under dehydrated state, $$(0.1-2)R_{2/n}O \cdot [aLa_2O_3 \cdot bCe_2O_3] \cdot ySiO_2$$

in which R is at least one mono- or divalent cation, n is the valence of R, M is at least one trivalent transition metal ion and/or aluminum ion, and $a+b=1$, $a \geq 0$, $b \geq 0$, and $y \geq 12$.

6 Claims, No Drawings

CRYSTALLINE SILICATES, AND PROCESSES FOR THE PRODUCTION OR USE THEREOF

This is a divisional of application Ser. No. 736,988, filed May 23, 1985, which in turn is a continuation of application Ser. No. 491,534, filed May 4, 1983, now abandoned.

BACKGROUND OF THE INVENTION

1. Field of the Invention

This invention relates to a novel crystalline silicate and a process for the production of the same, and further relates to a process for the production of hydrocarbons using this crystalline silicate. More particularly, it is concerned with a process for producing hydrocarbons such as aromatic hydrocarbons from alcohols, ethers or synthesis gas using the crystalline silicate as a catalyst.

2. Description of the Prior Art

The surroundings of petroleum playing the leading part of energy at present are very unstable and it has been feared that a "valley" of energy will come in the last half of 1980s to the 1990s due to deficiency of petroleum. To this end, it is required to practice economy in the consumption of petroleum in future and to use an alternative energy for petroleum such as coal, nuclear fuel, natural gas, etc. In particular, it has lately been watched with keen interest to develop the technique of C1-chemistry to make up for the short supply of gasoline, kerosene and gas oil which demands will relatively be expanded by producing them from other carbon sources than petroleum, e.g. coal and natural gas which can be found in abundance in the world.

Methods of producing hydrocarbons from coal can be classified mainly into two methods, i.e. direct method by liquefaction of coal and indirect method through the synthesis gas, and a number of studies have hitherto been made as to these two methods. The liquefaction of coal is generally carried out by subjecting coal to hydrogenation under a high pressure in the presence of a solvent to obtain gaseous or liquid hydrocarbons, but this method is still under development and unfavourable economically and the quality of the products is inferior to petroleum at present. On the other hand, the indirect method, which has already been put to practical use by SASOL in South Africa, consists in a method of converting a carbon source into hydrocarbons by preparing carbon monoxide and hydrogen in the presence of air, oxygen or steam and reacting them in the presence of a Fischer-Tropsch catalyst.

However, the use of the prior art Fischer-Tropsch catalyst such as fused iron or precipitated iron results in reaction products of hydrocarbons including paraffins and olefins, distributed widely from methane to wax and reaction products of various oxygen-containing compounds including alcohols, ethers, etc., and thus it is impossible to obtain selectively valuable products with a specified boiling point range. That is, the yield of the most valuable gasoline fraction is not sufficient and the gasoline fraction cannot be used as motor gasoline as such and should be modified, for example, by catalytic reforming, since it contains little aromatic hydrocarbons or highly branched paraffins or olefins and has low octane number.

The synthesis gas obtained from raw materials such as coal and natural gas can be converted into methanol in known manner, but methanol, as it is, has been used as only a raw material for chemicals at present, which use is considerably limited. Of late, however, a process for the synthesis of gasoline from methanol has been proposed by Mobil Oil Co. as disclosed in U.S. Pat. Nos. 3,894,103–3,894,107. The feature of this process consists in using zeolites of ZSM-5 series with an $SiO_2$/$Al_2O_3$ ratio of at least 12, different from the prior art zeolites, but in the case of using this catalyst, there arises a problem that several % or more of durene (1,2,4,5-tetramethylbenzene, mp 79° C.), causing plugging of a carburetor of engine, is formed as a byproduct and the catalyst is contaminated with carbon deposited so that its life is short. Furthermore, another process for the direct synthesis of gasoline from the synthesis gas using a mixed catalyst of the zeolite of ZSM-5 series and Fischer-Tropsch catalyst or methanol synthesis catalyst has been proposed by Mobil Oil Co. as disclosed in U.S. Pat. Nos. 4,096,163 and 4,157,338, but this process has also a drawback that a large quantity of carbon is deposited on the catalyst to shorten the life thereof.

SUMMARY OF THE INVENTION

It is an object of the present invention to provide a new crystalline silicate suitable for use as a catalyst for various organic reactions such as polymerization of organic compounds, alkylation, isomerization, disproportionation and the like.

It is another object of the present invention to provide a process for the production of the new crystalline silicate.

It is a further object of the present invention to provide a process for the production of hydrocarbons using the new crystalline silicate as a catalyst.

It is a still further object of the present invention to provide a process for the production of aromatic hydrocarbon mixtures using the crystalline silicate as a catalyst.

These objects can be attained by a crystalline silicate having a chemical composition represented by the general formula in the term of mole ratios of oxides under dehydrated state,

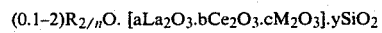

$(0.1-2)R_{2/n}O \cdot [aLa_2O_3 \cdot bCe_2O_3 \cdot cM_2O_3] \cdot ySiO_2$ in which R is one or more mono- or divalent cations, n is the valence of R, M is one or more trivalent transition metal ions and/or aluminum ion, and $a+b+c=1$, $a \geq 0$, $\geq 0$, $c \geq 0$, $a+b>0$ and $y \geq 12$.

DETAILED DESCRIPTION OF THE INVENTION

The inventors have made various efforts to solve the above described problems and consequently, have found a novel crystalline silicate which is suitable for use as a catalyst for the production of hydrocarbons from lower alcohols and/or ethers or for the production of hydrocarbons from the synthesis gas without substantial formation of aromatic hydrocarbons of $C_{10}$ or higher such as durene, whereby formation of carbon is suppressed to improve more its durability as compared with the prior art crystalline aluminosilicate catalyst of ZSM-5 series. This invention is based on our finding.

The prior art crystalline aluminosilicate described above is also called "zeolite" in which silica and alumina own jointly oxygen to hold a three-dimensional network structure, the ratio of oxygen atoms to the sum of aluminum atoms and silicon atoms is 2 and the negative electrovalence of $ALO_4$ tetrahedrons is balanced with alkali metal cations, in particular, sodium and potassium ions and in some case, with organo nitrogen cations.

Commercially available A-, X- and Y-type zeolites or mordenite have a silica to alumina ratio of at most 10 and the above described zeolite of ZSM-5 series is characterized by a silica to alumina ratio of at least 12. It is said that such a higher silica/alumina ratio serves to provide strongly acidic sites, from which conversion reaction of methanol into hydrocarbons proceeds.

On the other hand, the novel crystalline silicate found by the inventors is different from the above described crystalline aluminosilicate of the prior art and characterized by containing oxides of lanthanum, cerium and other transition metals which are considered to be effective for suppressing formation of carbon and improving the durability.

Accordingly, the present invention provides a crystalline silicate having a chemical composition represented by the general formula in the term of mole ratios of oxides under dehydrated state:

$$(0.1-2)R_{2/n}O \cdot [aLa_2O_3 \cdot bCe_2O_3] \cdot ySiO_2$$

in which R is at least one mono- or divalent cation, n is the valence of R, M is at least one trivalent transition metal ion and/or aluminum ion, and $a+b+c=1$, $a \geq 0$, $b \geq 0$, $c \geq 0$, $a+b > 0$ and $y \geq 12$.

In a preferred embodiment of the present invention, the crystalline silicate has a chemical composition represented by the general formula in the term of mole ratios of oxides under dehydrated state, $$(0.6-1.4)R_{2/n}O \cdot [aLa_2O_3 \cdot bCe_2O_3 \cdot M_2O_3] \cdot ySiO_2$$

in which R, a, b, c, y and n have the same meanings as described above.

In addition, the present invention provides a process for preparing the above described crystalline silicate.

Furthermore, the present invention provides a process for the production of hydrocarbons from alcohols and/or ethers each containing at most 4 carbon atoms per alkyl group using the above described crystalline silicate as a catalyst at a reaction temperature of 250° to 500° C. under a reaction pressure of at most 100 atm, and a process for the production of hydrocarbons from the synthesis gas using the above described crystalline silicate with a metal or metal compound having catalytic activity to hydrogenate carbon monoxide (hereinafter referred to as "carbon monoxide reducing catalyst") at a reaction temperature of 200° to 500° C. under a reaction pressure of at most 300 atm.

The above described crystalline silicate of the present invention can be synthesized by hydrothermal reaction of a reaction mixture comprising the following silica source, lanthanum and/or cerium source, transition metal and/or alumina source, alkali source, water and organic compound containing nitrogen or oxygen, optionally with an acid to control the pH.

As the silica source, there can be used any silica or silica compounds commonly used in the synthesis of zeolites, for example, silica powder, colloidal silica and silicates such as water glass.

As the lanthanum, cerium and transition metal sources, there can be used sulfates, nitrates, chlorides and other salts of lanthanum, cerium and transition metals. By the term "trivalent transition metal ion (M)" in this specification and in the claiming clauses, we mean trivalent cations of Group VIII elements such as iron, cobalt, rhodium, ruthenium and palladium, rare earth elements such as lanthanum and cerium and other elements such as titanium, vanadium, chromium, niobium, tantalum, antimony and the like.

As the alumina source, there can be used chloride, nitrate, sulfate, oxide and hydroxide of aluminum and above all, sodium aluminate is most preferable.

As the alkali source, there can be used hydroxides and other compounds such as aluminates and silicates of alkali metals such as sodium and alkaline earth metals such as calcium, and salts thereof such as sodium chloride.

As the organic compound containing nitrogen or oxygen, there can be used the following organic compounds given without limiting the same:

(1) Organic Amines
primary amines such as n-propylamine, monoethanolamine and the like; secondary amines such as dipropylamine, diethanolamine and the like; tertiary amines such as tripropylamine, triethanolamine and the like; other amines such as ethylenediamine, diglycolamine and the like; mixtures of these compounds with halogenated hydrocarbons such as propyl bromide; and quaternary ammonium salts such as tetrapropylammonium salt and the like (2) Organic Nitrogen Compounds other than Organic Amines
nitrogen-containing hetrocyclic compounds such as pyridine, pyrazine, pyrazole and the like (3) Alcohols or Mixtures thereof with Ammonia
monoalcohols such as ethanol; diols such as ethylene glycol and the like; mixtures of these alcohols with ammonia By the term "mono- or divalent cation (R)" in this specification and in the claiming clauses, we mean alkali metal ions, alkaline earth metal ions, ions of the above described organic compounds and hydrogen ion formed by calcining or ion exchange treatment.

The crystalline silicate of the present invention has a structure characterized by replacing a part of all of Al in the prior art zeolite structure by lanthanum, cerium or other transition metals and further has an $SiO_2/(La_2O_3+Ce_2O_3+M_2O_3)$ ratio of at least 12, which is generally prepared from a reaction mixture having the following mole composition:

$SiO_2/(La_2O_3+Ce_2O_3+M_2O_3)$: 12–3000 (preferably 20–200)
$OH^-/SiO_2$: 0–1.0 (preferably 0.2–0.8)
$H_2O/SiO_2$: 2–1000 (preferably 10–200)
organic compound/$(La_2O_3+Ce_2O_3+M_2O_3)$: 1–100 (preferably 5–50)

The crystalline silicate of the present invention can be synthesized by heating the above described raw materials at a sufficient temperature for a sufficient time to form the crystalline silicate. Generally, the hydrothermal synthesis temperature is 80°–300° C., preferably 130°–200° C. and the hydrothermal synthesis time is 0.5–14 days, preferably 1–10 days. The pressure is not particularly limited, but the hydrothermal reaction is preferably carried out under autogenous pressure.

The hydrothermal synthesis reaction is carried out by heating raw material mixture at a desired temperature, optionally with stirring, and continued until a crystalline silicate is formed. After the crystal is formed, the reaction mixture is cooled to room temperature, filtered, washed with water, and ordinarily, dried at 100° C. or higher for 5 to 24 hours.

The crystalline silicate of the present invention is a porous crystalline material with a regular and constant crystalline structure, which has generally X-ray diffraction pattern shown in Table 1:

TABLE 1

| 2θ | I/Io |
|---|---|
| 7.9 ± 0.1 | VS |
| 8.8 ± 0.1 | VS |
| 13.2 ± 0.2 | W |
| 13.9 ± 0.2 | M |
| 14.7 ± 0.2 | M |
| 15.4 ± 0.2 | W |
| 15.9 ± 0.2 | M |
| 19.3 ± 0.2 | W |
| 20.8 ± 0.2 | M |
| 23.1 ± 0.2 | S |
| 23.8 ± 0.1 | M |
| 26.9 ± 0.3 | M |
| 29.2 ± 0.2 | W |
| 29.9 ± 0.2 | M |

Note: W = weak, M = medium, S = strong, VS = very strong

To obtain the above described data of Table 1 was used the standard technique using Kd doublet of copper for irradiation. Io is the intensity of the strongest peak, I/Io being a relative intensity.

When using this crystalline silicate as a catalyst, it is desirable to subject to previous activation by heating at a temperature of 400° to 700° C. in the air for 2 to 48 hours, but this previous activation is not always required because the crystalline silicate can be activated under reaction heating condition.

The alkali metal present in this crystalline silicate can be exchanged in conventional manner with at least one of other cations such as hydrogen, iron, rhodium, ruthenium, gallium and the like to give a hydrogen-type or other corresponding ion type. For example, the ion exchange into H-type can be carried out by a method comprising calcining the crystalline silicate prepared as described above to remove the organic compound and then immersing in a strong acid such as hydrochloric acid to convert directly into H-type, or a method comprising immersing the crystalline silicate in an aqueous solution of an ammonium compound to convert into $NH_4$-type and then calcining to give H-type. On the other hand, a crystalline silicate of metallic cation type can be obtained by immersing a crystalline silicate in an aqueous solution of a chloride or nitrate of metal to be ion exchanged and heating at a temperature of 50° to 100° C. for 3 hours to several days. The above described crystalline silicates of H-type and metallic cation type will hereinafter be referred to as "activated crystalline silicate".

The crystalline silicate or activated crystalline silicate, used as a catalyst, can be impregnated with one or more metal compounds which include those of copper, zinc, chromium, lead, antimony, bismuth, titanium, vanadium, manganese, iron, cobalt, nickel, ruthenium, rhodium, palladium, platinum, lanthanum and cerium.

The thus impregnated silicate contains one or more metal oxides in a proportion of preferably 0.1 to 5.0 % by weight. The metal compounds used herein are, for example, nitrates or chlorides which are soluble in water and capable of giving the corresponding oxides through heating and decomposing. Accordingly, a mixture of the crystalline silicate or activated crystalline silicate with a metal compound is prepared by impregnating the former with an aqueous solution of the latter, followed by drying and calcining.

The catalyst obtained in this way has a higher catalytic activity in organic reactions for production of hydrocarbons from alcohols and/or ethers having 4 or less carbon atoms per alkyl group, such as methanol and dimethyl ether, polymerization, alkylation, isomerization, disproportionation, etc. of organic compounds, than the prior art catalysts.

The crystalline silicate or activated crystalline silicate of the present invention exhibits a very excellent catalytic activity in organic reactions including carbonium ion as an intermediate. These reactions are generally carried out by bringing an organic compound or a raw material containing the organic compound into contact with the crystalline silicate or activated crystalline silicate of the present invention at a temperature of 40° to 700° C., a pressure of 200 atm or lower and a weight hourly space velocity (referred to as "WHSV") of 0.1 to 1000 $h^{-1}$.

More particularly, where the above described conversion reaction is polymerization of raw materials containing olefins, the conditions are a temperature of 260° to 500° C., pressure of 50 atm or lower and WHSV of 0.5 to 50 $h^{-1}$. Where the above described conversion reaction is alkylation of aromatic compounds such as benzene and toluene with olefins or alcohols, the reaction conditions are a temperature of 200° to 550° C., pressure of 60 atm or lower, WHSV of 0.5 to 50 $h^{-1}$ and aromatic compound/alkylating agent mole ratio of 2 to 20. Where the above described conversion reaction is isomerization of aromatic compounds such as xylene, the reaction conditions are a temperature of 150° to 500° C., pressure of 60 atm or less and WHSV of 0.2 to 100 $h^{-1}$. Where the above described conversion reaction is isomerization of paraffins or olefins, the reaction conditions are a temperature of 40° to 400° C., pressure of 60 atm or lower and WHSV of 0.1 to 20 $h^{-1}$. Where the above described conversion reaction is disproportionation of aromatic compounds such as toluene, the reaction conditions are a temperature of 300° to 600° C., pressure of at most 100 atm and WHSV of 0.5 to 20 $h^{-1}$.

Furthermore, the crystalline silicate or activated crystalline silicate of the present invention can also be applied to catalytic dewaxing using the shape selectivity thereof. In this case, the reaction conditions are a temperature of 200° to 500° C., pressure of 100 atm or lower and WHSV of 0.1 to 20 $h^{-1}$.

In particular, the crystalline silicate or activated crystalline silicate of the present invention has a much higher catalytic activity in reactions of synthesizing aromatic compounds or lower olefins from alcohols and/or ethers containing 4 or less carbon atoms per alkyl group. Useful examples of the alcohols and/or ethers containing 4 or less carbon atoms per alkyl group are methanol, ethanol, n-propanol, isopropanol, n-butanol, isobutanol, sec-butanol and tert-butanol, and ether compounds of $C_1$–$C_4$ such as dimethyl ether. These alcohols and ethers can be used individually or in combination.

Limitation of the reaction conditions to as above is based on the following reasons:

The reason of limiting the reaction temperature to 250° to 600° C. is that if the reaction temperature is lower than 250° C., alcohols or ethers scarcely react, while if higher than 600° C., the rates of coking reaction of alcohols or ethers and decomposition into carbon monoxide or hydrogen are increased to shorten the life of the catalyst. The reason of limiting the reaction pressure to 100 atm or less is that if the pressure is higher than 100 atm, alkylation of aromatic hydrocarbons proceeds excessively to increase the ratio of aromatic hydrocarbons of $C_{10}$ or higher, e.g. durene, causing the foregoing problem when used as gasoline, and the conversion efficiency of the reaction is not increased in spite of the increased reaction pressure.

By the term "aromatic hydrocarbon mixtures" in this specification and in the claiming clauses, we mean hydrocarbon mixtures containing preferably at least 1% by weight of aromatic hydrocarbons and other aliphatic hydrocarbons (paraffins and olefins).

The mixed catalyst of the crystalline silicate or activated crystalline silicate with the carbon monoxide reducing catalyst according to the present invention has a much higher catalytic activity in reactions of synthesizing hydrocarbons from the synthesis gas.

Limitation of the reaction conditions to as described above is based on the following reasons:

The reason of limiting the reaction temperature to 200° to 500° C. is that if the reaction temperature is lower than 200° C., the hydrogenation reaction rate of carbon monoxide is too small to obtain a sufficient conversion, while if higher than 500° C., the hydrocarbon synthesis reaction through hydrogenation reaction of carbon monoxide is disadvantageous in respect of free energy and thus the resulting hydrocarbons consist substantially of methane.

The reason of limiting the reaction pressure to 300 atm or lower is that if the reaction pressure is higher than 300 atm, carbon deposition reaction (200—C+ $CO_2$) tends to take place often and the conversion efficiency of the reaction is not so increased in spite of the increased reaction pressure.

The synthesis gas used in the present invention can be prepared from fossil fuels by any known method. The fossil fuels used herein include anthracite, bituminous coal, brown coal, crude oil, shale oil, tar sand oil, natural gas, coked coal, petroleum coke, gas oil, distillation residue and the like. These fuels can be used individually or in combination. Of course, other carbonaceous fuels such as peat, wood and cellulose wastes can be used.

Raw synthesis gases prepared from fossil fuels contain various impurities such as sulfur compounds and metal carbonyl compounds and are generally characterized by the hydrogen to carbon oxides ratio depending upon fossil fuels used and the gasification technique. In general, it is preferable for the efficiency of the subsequent conversion process to purify the raw synthesis gas by removing impurities. The technique for this purification has well been known.

In addition, if required, the synthesis gas is preferably subjected to control of the hydrogen to gaseous carbon oxides volume ratio to 0.2 to 6.0 before use in the present invention. When the purified synthesis gas is excessively rich in carbon oxides, the above described ratio can be adjusted to a suitable range by the well-known water gas shift reaction.

When the synthesis gas contains hydrogen in excess, on the other hand, the above described ratio can be adjusted to a suitable range by addition of carbon dioxide or carbon monoxide.

Moreover, there can also be used synthesis gases containing components in addition to hydrogen or carbon monoxide, for example, mixtures of carbon monoxide and steam and mixtures of carbon dioxide and hydrogen. In the production of hydrocarbon mixtures rich in aromatic hydrocarbons, in particular, hydrogen donors such as lower hydrocarbons, lower alcohols alcohols and lower ethers can be fed with the synthesis gas.

The carbon monoxide reducing catalyst used in the present invention can be selected from any of catalysts well known in the art as those for the production of hydrocarbons, oxygen-containing organic substances and mixtures thereof from the synthesis gas, for example, from the methanol synthesis catalysts, Fischer-Tropsch catalysts and their modified catalysts. The methanol synthesis catalyst includes combinations of chromium oxide with metallic zinc or metallic copper, chromium oxide with ainc oxide or copper oxide, alumina with metallic zinc or metallic copper and alumina with zinc oxide or copper oxide, and further improved catalysts thereof. In fact, the synthesis gas is subject to conversion on these various catalysts under conditions of a reaction temperature of 150° to 500° C. and a reaction pressure of 1000 atm or less to thus form carbon monoxide-reduced products such as alcohols and hydrocarbons. The active component of the carbon monoxide reducing catalyst is a metal selected from the group consisting of Group IB, IIB, IIIB, IVB, VB, VIB, VIIB and VIII elements of Periodic Table, or an oxide thereof, individually or in combination. Illustrative of the metal or oxide are copper, zinc, titanium, zirconium, chromium, vanadium, manganese, iron, cobalt, nickel, ruthenium, thorium and rhodium, and oxides thereof. In addition, alkali metals, alkaline earth metals and rare earth metals or compounds of these metals can preferably be used as an accelerating agent and supports such as alumina, silica, titania and diatomaceous earth can also be used.

The mixed catalyst of the crystalline silicate or activated crystalline silicate with the carbon monoxide reducing catalyst according to the present invention can be prepared by various methods. For example, the carbon monoxide reducing catalyst and crystalline silicate or activated crystalline silicate are separately formed into catalytic grains such as pellets or extruded ones and then mixed in a suitable proportion, or both are ground into powders, mixed in a suitable proportion and formed into pellets or extruded ones. During the mixing, a binder such as clay can be added to the mixture. As another method, the crystalline silicate can be impregnated or ion exchanged with a component having a catalytic reducing activity of carbon monoxide in the form of its desired metal salt, then dried and calcined, thereby combining the crystalline silicate with the component. In a further method of intimately mixing them, a carbon monoxide reducing component is precipitated in the presence of the crystalline silicate.

The carbon monoxide reducing catalyst to crystalline silicate or activated crystalline silicate ratio is not particularly limited, but its preferable range is 0.1:100 to 100:1 by weight.

The present invention will be explained in detail with reference to the following examples. It will be obvious to those skill in the art that various changes and modifications can be made in components, ratios, operational orders and the like without departing from the spirit of the present invention. Therefore, the present invention should not be construed as being limited to the following examples.

EXAMPLE 1

A crystalline silicate was synthesized by the following procedures: Water glass, lanthanum chloride, cerium chloride and water were mixed to give a mole ratio of $36Na_2O.(0.5La_2O_3.0.5Ce_2O_3).80SiO_2.1600H_2O$, to which a suitable quantity of hydrochloric acid was added to adjust the pH of the mixture to about 9 and tripropylamine and propyl bromide as an organic compound were then added in a quantity of 20 times the moles of the sum of $La_2O_3$ and $Ce_2O_3$ with mixing adequately, and the resultant mixture was charged in a 500 ml stainless autoclave.

The above described mixture was subjected to reaction at 160° C. for 3 days with stirring at about 500 rpm, cooled, filtered to separate a solid component, washed adequately with water until the pH of the washing water be about 8, dried at 110° C. for 12 hours and then calcined at 550° C. for 3 hours.

This product had a crystal particle size of about 1 μm and a chemical composition in the term of moles of oxides under dehydrated state and exclusive of the organic compound:

$$0.4Na_2O.(0.5La_2O_3.0.5Ce_2O_3).80SiO_2$$

This will hereinafter be referred to as "Crystalline Silicate 1".

Similar crystalline silicates were obtained also in the case of using nitric acid instead of the hydrochloric acid, using lanthanum nitrate instead of the lanthanum chloride or using silica sol instead of the water glass, when synthesizing Crystalline Silicate 1. When the reaction was carried out at 170° C. or 180° C. for 2 days instead of the above described hydrothermal synthesis condition (160° C., 3 days), a similar crystalline silicate was also obtained.

The procedure for preparing Crystalline Silicate 1 was repeated except changing the quantity of lanthanum chloride and cerium chloride in mixing the raw materials for Crystalline Silicate 1 as shown in Table 2 in the term of mole ratios of $La_2O_3$ and $Ce_2O_3$, thus preparing Crystalline Silicates 2 to 6 as shown in Table 2:

TABLE 2

| Crystalline Silicate No. | Mole Ratios in Mixing Raw Materials | | Composition of Crystalline Silicate Exclusive of Organic Compound (dehydrated state) |
|---|---|---|---|
| | $La_2O_3$ | $Ce_2O_3$ | |
| 2 | 1 | 0 | $0.4Na_2O.La_2O_3.80SiO_2$ |
| 3 | 0.9 | 0.1 | $0.4Na_2O.(0.9La_2O_3.0.1Ce_2O_3).80SiO_2$ |
| 4 | 0.6 | 0.4 | $0.4Na_2O.(0.6La_2O_3.0.4Ce_2O_3).80SiO_2$ |
| 5 | 0.3 | 0.7 | $0.4Na_2O.(0.3La_2O_3.0.7Ce_2O_3).80SiO_2$ |
| 6 | 0 | 1 | $0.4Na_2O.Ce_2O_3.80SiO_2$ |

Crystalline Silicates 7 to 13 and 24 were prepared by repeating the procedure for the preparation of Crystalline Silicate 3 except using ferric chloride, ruthenium chloride, neodymium chloride, titanium chloride, vanadium chloride, chromium chloride, antimony chloride or aluminum chloride in a quantity of the same mole of oxide as $Ce_2O_3$. These crystalline silicates had a chemical composition represented by the general formula in the term of mole ratios of oxides under dehydrated state and exclusive of the organic compound, $$(0.3-0.5)Na_2O.(0.9La_2O_3.0.1M_2O_3).80SiO_2$$

in which M is Fe, Ru, Nd, Ti, V, Cr, Sb or Al in the order of Crystalline Silicates 7–13 and 24.

Crystalline Silicates 14 to 20 were prepared by repeating the procedure for the preparation of Crystalline Silicate 1 except using organic compounds as shown in Table 3 in a quantity of 20 times the mole of lanthanum oxide:

TABLE 3

| Crystalline Silicate No. | Organic Compound |
|---|---|
| 14 | monoethanolamine |
| 15 | ethanolamine, propyl bromide |
| 16 | diethanolamine |
| 17 | triethanolamine |
| 18 | diglycolamine |
| 19 | butylamine, butyl bromide |
| 20 | tetrapropylammonium bromide |

These Crystalline Silicates 14 to 20 had a chemical composition in the term of mole ratios of oxides under dehydrated state.

$$(0.1-0.6)Na_2O.(0.5La_2O_3.0.5Ce_2O_3).80SiO_2$$

Crystalline Silicates 21 to 23 were prepared by repeating the procedure for the preparation of Crystalline Silicate 2 except changing the $SiO_2/La_2O_3$ ratio in 20, 200 and 400.

It was found that the above described Crystalline Silicates 1 to 24 were crystalline materials each having an X-ray diffraction pattern satisfying that of Table 1 and an $SiO_2$ content of 90% by weight or more.

COMPARATIVE EXAMPLE 1

The procedure of Example 1 was repeated except that aluminum chloride was used in place of the lanthanum chloride and cerium chloride and mixed with the other same materials to give a mole ratio of $36Na_2O.Al_2O_3.80SiO_2.1600H_2O$, to which a suitable quantity of hydrochloric acid was added to adjust the pH of the mixture to about 9 and tetrapropylammonium bromide as an organic compound was added in a quantity of 20 times the mole of $Al_2O_3$, thus obtaining an aluminosilicate having a chemical composition in the term of mole ratios of oxides under dehydrated state and exclusive of the organic compound, $$0.5Na_2O.Al_2O_3.80SiO_2$$

and having the same X-ray powder diffraction pattern as ZSM-5 described in U.S. Pat. No. 3,702,886. The product obtained in this Comparative Example 1 will hereinafter be referred to as "ZSM-5".

EXAMPLE 2

The crystalline silicates synthesized in Example 1 and the zeolite ZSM-5 synthesized in Comparative Example 1 were immersed in 1N hydrochloric acid and allowed to stand at 80° C. for 7 days, then washed, filtered, dried at 110° C. for 12 hours, calcined at 550° C. and shaped into a size of 1–3 mm to obtain catalysts.

Methanol was brought into contact with the thus obtained catalysts under reaction conditions of normal pressure, a temperature of 370° C., and an LHSV (liquid hourly space velocity) of 2 $h^{-1}$ to obtain results as shown in Table 4.

In addition, Crystalline Silicate 1A, synthesized using silica sol instead of the water glass respectively in the above described procedures, were treated and then contacted with methanol in an analogous manner to described above, thus obtaining the same result as in the case of Crystalline Silicate 1 shown in Table 4.

TABLE 4

| Crystalline Silicate No. | Methanol Conversion (%) | Composition of Hydrocarbon Products (wt %) | | | Ratio of Durene in Hydrocarbon Products C$_{5+}$ (wt %) |
|---|---|---|---|---|---|
| | | C$_1$-C$_4$ | C$_5$-C$_{10}$ Aliphatic Hydrocarbon* | Aromatic Hydrocarbons | |
| 1 | 99.5 | 29 | 49 | 22 | 0.3 |
| 2 | 99.5 | 35 | 46 | 19 | 0.2 |
| 6 | 99.5 | 27 | 49 | 24 | 0.4 |
| 7 | 99.5 | 24 | 50 | 26 | 0.4 |
| 9 | 99.5 | 32 | 48 | 20 | 0.3 |
| 11 | 99.5 | 30 | 48 | 22 | 0.3 |
| 13 | 99 | 32 | 49 | 19 | 0.2 |
| 14 | 97 | 37 | 46 | 17 | 0.2 |
| 18 | 98 | 35 | 47 | 18 | 0.2 |
| 20 | 99.5 | 28 | 50 | 22 | 0.3 |
| 22 | 99.5 | 37 | 47 | 16 | 0.2 |
| 24 | 99.5 | 23 | 49 | 28 | 0.5 |
| Comparison ZSM-5 | 99 | 38 | 26 | 36 | 3.4 |

Note: *C$_5$-C$_{10}$ Aliphatic hydrocarbons include naphthenes. This applies correspondingly to the following examples.

EXAMPLE 3

Using a catalyst obtained by treating Crystalline Silicate 1 synthesized in Example 1 in an analogous manner to Example 2, methanol was converted under normal pressure at various temperatures and LHSV as shown in Table 5 to thus obtain results shown in Table 5:

TABLE 5

| Reaction Temperature (°C.) | L.H.S.V. (h$^{-1}$) | Methanol Conversion (%) | Composition of Hydrocarbon Products (wt %) | | | Ratio of Durene in Hydrocarbons Products C$_{5+}$ (wt %) |
|---|---|---|---|---|---|---|
| | | | C$_1$-C$_4$ | C$_5$-C$_{10}$ Aliphatics | Aromatics | |
| 350 | 2 | 99 | 28 | 46 | 26 | 0.5 |
| 400 | 2 | 100 | 31 | 46 | 23 | 0.3 |
| 500 | 2 | 100 | 41 | 39 | 20 | 0.1 |
| 550 | 2 | 100 | 84 | 8 | 8 | 0.1 |
| 370 | 5 | 97 | 40 | 41 | 19 | 0.08 |
| 370 | 10 | 94 | 59 | 26 | 15 | 0.03 |

As is seen from these results, methanol was sufficiently converted into hydrocarbons under the above described conditions.

In the activity tests of varying LHSV, the proportion of olefins in C$_1$-C$_4$ hydrocarbons is 41% by weight at 350° C., 70% by weight at 400° C., 84% by weight at 500° C. and 93% by weight at 550° C. in the case of an LHSV of 2 h$^{-1}$, 78% by weight at 370° C. in the case of an LHSV of 5 h$^{-1}$ and 91% by weight at 370° C. in the case of an LHSV of 10 h$^{-1}$. This is due to that the reaction contact time is shortened by increasing LHSV so that lower olefins as intermediate products in the synthesis reaction of aromatic hydrocarbons from methanol are increased.

According to the present invention, therefore, not only gasoline containing aromatic hydrocarbons but also lower olefins such as ethylene useful as a raw material in chemical industry one effectively be produced from alcohols and others.

Then, tests were carried out by changing the reaction pressure while keeping constant the temperature (370° C.) and LHSV (2 h$^{-1}$) to thus obtain results as shown in Table 6:

TABLE 6

| Reaction Pressure (Kg/cm$^2$) | Methanol Conversion (%) | Composition of Hydrocarbon Products (% by weight) | | | Ratio of Durene in Hydrocarbon Products C$_{5+}$ (% by weight) |
|---|---|---|---|---|---|
| | | C$_1$-C$_4$ | C$_5$-C$_{10}$ Aliphatic Hydrocarbon | Aromatic Hydrocarbons | |
| 10 | 100 | 26 | 42 | 32 | 0.8 |
| 40 | 100 | 23 | 41 | 36 | 2.1 |

As is evident from these results, methanol was sufficiently converted into hydrocarbons under the above described reaction conditions. The proportion of aromatic hydrocarbons tends to be increased with the increase of the reaction pressure.

EXAMPLE 4

Crystalline Silicate 2 synthesized in Example 1 was treated in an analogous manner to Example 2, and further immersed in an aqueous solution of iron nitrate, followed by treatment at 100° C. for 6 hours, to give an ion exchange quantity as shown in Table 7, or further immersed in an aqueous solution of potassium nitrate, followed by treatment at 100° C. for 6 hours, to give an ion exchange quantity as shown in Table 7, thus obtaining respectively Catalysts 1 and 2. Using these catalysts, methanol was converted into hydrocarbons under the same reaction corditions as Example 2, to thus obtain results shown in Table 7:

TABLE 7

| Catalyst No. | Ion Exchange Quantity (wt %) | Methanol Conversion (%) | Composition of Hydrocarbon Products (wt %) | | | Ratio of Durene in Hydrocarbon Products C$_{5+}$ (wt %) |
|---|---|---|---|---|---|---|
| | | | C$_1$-C$_4$ | C$_5$-C$_{10}$ Aliphatics | Aromatics | |
| 1 | Fe 0.5 | 100 | 25 | 46 | 29 | 0.3 |
| 2 | Ga 0.5 | 100 | 24 | 48 | 28 | 0.3 |

EXAMPLE 5

Crystalline silicate 1 synthesized in Example 1 was treated in an analogous manner to Example 2 to prepare a catalyst. Using this catalyst, alcohols and ethers as shown in Table 8 were converted into hydrocarbons under reaction conditions of normal pressure, a temperature of 370° C. and LHSV of 2 h$^{-1}$ to thus obtain results as shown in Table 8:

TABLE 8

| Raw Material | Conversion (%) | Composition of Hydrocarbon Products (wt %) | | |
|---|---|---|---|---|
| | | $C_1$–$C_4$ | $C_5$–$C_{10}$ Aliphatic Hydrocarbons | Aromatic Hydrocarbon |
| Ethanol | 99 | 34 | 46 | 20 |
| n-Propanol | 98 | 32 | 49 | 19 |
| Dimethyl Ether | 100 | 26 | 50 | 24 |
| Diethyl Ether | 100 | 30 | 48 | 22 |

EXAMPLE 6

Crystalline Silicate 1 synthesized in Example 1 and the zeolite ZSM-5 synthesized in Comparative Example 1 were treated in an analogous manner to Example 2 and contacted with methanol under the same reaction conditions for a long time.

Consequently, ZSM-5 started to be deactivated when 300 g of methanol was processed per 1 g of the catalyst, while Crystalline Silicate 1 was not deactivated until 600 g of methanol was processed per 1 g of the catalyst

EXAMPLE 7

Crystalline Silicate 2 synthesized in Example 1 was treated in an analogous manner to Example 2 to prepare a catalyst. 150 g of this catalyst was added to a solution containing 384.6 g of cerium nitrate (containing 39 wt % of $Ce_2O_3$) in 2000 ml of water, to which aqueous ammonia was added with stirring well to a pH of 8.3, and gelatinized. This mixed gel was filtered, washed with water until the nitrate was not found in the washing water, dried at 130° C. and then calcined at 500° C. for 3 hours to prepare a Catalyst 3. When methanol was converted into hydrocarbons using Catalyst 3 under the same reaction conditions as Example 2, there were obtained results of methanol conversion 99.5%; and composition of $C_1$–$C_4$ 26 wt %, $C_5$–$C_{10}$ aliphatic hydrocarbons 47 wt % and aromatic hydrocarbon on 27 wt %.

EXAMPLE 8

Crystalline silicate 2 synthesized in Example 1 was treated in an analogous manner to Example 2 to prepare a catalyst. This catalyst was mixed with alumina sol and calcined to prepare a Catalyst 4 consisting of 50% by weight of the crystalline silicate and 50% by weight of $A_2O_3$, while the catalyst was mixed with alumina boehmite gel instead of the alumina sol and calcined to prepare a Catalyst 5 consisting of 50% by weight of the crystalline silicate and 50% by weight of $Al_2O_3$.

Using Catalysts 4 and 5, methanol was converted under the same reaction conditions as Example 2, thus obtaining results as shown in Table 9.

EXAMPLE 9

In the preparation of Catalyst 4 and 5 in Example 8, the mixed slurry of the crystalline silicate and alumina sol or alumina boehmite gel was respectively subjected to spraying drying at about 150° C. to give a mean particle size of 50 μm and thereafter calcined to prepare Catalysts 6 and 7. Using Catalysts 6 and 7 under fluidized, methanol was converted at 370° C. and an LSHV of 2 $h^{-1}$ to thus obtain results as shown in Table 9:

TABLE 9

| Example No. | Reaction Pressure (Kg/cm²G) | Catalyst No. | Methanol Conversion (%) | Composition of Hydrocarbon Products (wt %) | | | Ratio of Durene in Hydrocarbon Products $C_{5+}$ (wt %) |
|---|---|---|---|---|---|---|---|
| | | | | $C_1$–$C_4$ | $C_5$–$C_{10}$ Aliphatics | Aromatics | |
| 8 | 0 | 4 | 99 | 32 | 48 | 20 | 0.2 |
| | | 5 | 99 | 33 | 45 | 22 | 0.3 |
| 9 | 0 | 6 | 98 | 34 | 47 | 19 | 0.2 |
| | 10 | | 97 | 22 | 49 | 29 | 0.7 |
| | 0 | 7 | 99 | 33 | 46 | 21 | 0.2 |
| | 10 | | 98 | 19 | 50 | 31 | 0.9 |

EXAMPLE 10

Using a catalyst obtained by synthesizing Crystalline Silicate 1 in an analogous manner to Example 1 and activating in an analogous manner to Example 2, experiments were carried out as to reactions as shown in Table 10 and there were obtained results as shown in Table 10:

TABLE 10

| | Reaction Temperature (°C.) | WHSV ($h^{-1}$) | Conversion (%) | Composition of Hydrocarbon Products | | |
|---|---|---|---|---|---|---|
| | | | | $C_1$–$C_4$ | $C_5$–$C_{10}$ Aliphatic Hydrocarbons | Aromatic Hydrocarbons |
| (1) Conversion of Propylene | 390 | 2 | 99 | 32 wt % | 39 wt % | 29 wt % |
| (2) Alkylation of Toluene with Methanol | 390 Toluene/Methanol ≈1.5 | 2 | Conversion of Toluene 64 | Yield of Xylene 41%- Ratio of Resulting Xylene Isomers (p: 49%; m: 28%; o: 23%) | | |
| (3) Alkylation of Benzene with Ethylene | 390 Benzene/Ethylene ≈5 | 9 | Conversion of Ethylene 99 | Yield of Ethylbenzene 99% (Byproducts: Diethylbenzene, etc.) | | |
| (4) Disproportionation of Toluene | 450 | 30 | 16 | Xylene (p: 4.1%; m: 2.6%; o: 1.4%) Benzene 7.1% Residue: Toluene | | |
| (5) Isomerization | 430 | 2 | 48 | Ratio of Resulting Xylene | | |

TABLE 10-continued

| | Reaction Temperature (°C.) | WHSV (h$^{-1}$) | Conversion (%) | Composition of Hydrocarbon Products |
|---|---|---|---|---|
| of Xylene | | | | Isomers (p: 24%; m: 52%; o: 24%) |

EXAMPLE 11

A methanol synthesis catalyst consisting of 75% by weight of zinc oxide and 25% by weight of chromium oxide was mixed with H-type Crystalline Silicates 1–13 and 24 in a proportion by weight of 80:20 and pelletized to prepare Mixed Catalysts S-1 to S-13 corresponding to Crystalline Silicates 1–13 and Mixed Catalyst S-37 corresponding to Crystalline Silicate 24.

These catalysts were respectively contacted with a mixed gas of hydrogen and carbon monoxide ($H_2/CO=1$) under conditions of a pressure of 50 Kg/cm$^2$ abs., a temperature of 400 °C. and a GHSV (gas hourly space velocity) of 1000 h$^{-1}$ to obtain results as shown in Table 11:

TABLE 11

| Catalyst No. | CO Conversion (%) | Composition of Hydrocarbon Products (wt %) | | | |
|---|---|---|---|---|---|
| | | CH$_4$ | C$_2$-C$_4$ | C$_5$-C$_{10}$ Aliphatic Hydrocarbons | Aromatic Hydrocarbons |
| S-1 | 70 | 6 | 23 | 22 | 49 |
| S-2 | 68 | 5 | 21 | 23 | 51 |
| S-3 | 68 | 5 | 21 | 23 | 51 |
| S-4 | 70 | 6 | 23 | 22 | 49 |
| S-5 | 70 | 6 | 23 | 22 | 49 |
| S-6 | 73 | 8 | 25 | 20 | 47 |
| S-7 | 81 | 10 | 27 | 26 | 37 |
| S-8 | 85 | 13 | 29 | 28 | 30 |
| S-9 | 68 | 5 | 20 | 23 | 52 |
| S-10 | 69 | 6 | 21 | 22 | 51 |
| S-11 | 72 | 8 | 22 | 22 | 48 |
| S-12 | 70 | 6 | 25 | 20 | 49 |
| S-13 | 70 | 7 | 23 | 22 | 48 |
| S-37 | 76 | 12 | 27 | 25 | 36 |

When as to Crystalline Silicate 1A synthesized by the use of silica sol instead of water glass in the preparation of Crystalline Silicate 1, a mixed catalyst was prepared in an analogous manner to described above and brought into contact with a mixed gas of hydrogen and carbon monoxide under the same conditions as described above, there were obtained similar results to those in the case of Catalyst S-1 shown in Table 11.

EXAMPLE 12

An iron oxide catalyst commonly used as a predominant component in a Fischer-Tropsch synthesis catalyst was mixed with Crystalline Silicates 14–23 of Example 1 in the same proportion by weight and pelletized to prepare Mixed Catalysts S-14 to S-23 corresponding to Crystalline Silicates 14 to 23.

These catalysts were respectively contacted with a mixed gas of hydrogen and carbon monoxide ($H_2/CO=1$) under conditions of a pressure of 20 Kg/cm$^2$ abs., a temperature of 300° C. and a GHSV of 1000 h$^{-1}$ to obtain results as shown in Table 12:

TABLE 12

| Catalyst No. | CO Conversion (%) | Composition of Hydrocarbon Products (wt %) | | | |
|---|---|---|---|---|---|
| | | CH$_4$ | C$_2$-C$_4$ | C$_5$-C$_{10}$ Aliphatic Hydrocarbons | Aromatic Hydrocarbons |
| S-14 | 83 | 27 | 28 | 24 | 21 |
| S-15 | 84 | 26 | 28 | 25 | 21 |
| S-16 | 83 | 27 | 28 | 24 | 21 |
| S-17 | 85 | 26 | 27 | 23 | 24 |
| S-18 | 85 | 26 | 27 | 23 | 24 |
| S-19 | 89 | 26 | 27 | 23 | 24 |
| S-20 | 90 | 27 | 27 | 22 | 24 |
| S-21 | 86 | 25 | 26 | 25 | 24 |
| S-22 | 83 | 27 | 28 | 24 | 21 |
| S-23 | 79 | 31 | 26 | 26 | 15 |

EXAMPLE 13

Crystalline Silicate 1 synthesized in Example 1 was mixed with carbon moroxide reducing catalysts as shown in the following table in the same proportion by weight and pelletized to prepare Mixed Catalysts S-24 to S-30.

These catalysts were respectively contacted with a mixed gas of hydrogen and carbon monoxide ($H_2/CO=1$) under conditions of a pressure of 20 Kg/cm$^2$ abs., a temperature of 300 °C. and a GHSV of 1000 h$^{-1}$ to obtain results as shown in Table 13. Mixed Catalyst S-30 was subjected to this test under a pressure of 40 Kg/cm$^2$.

Table 13

| Catalyst No. | CO Reducing Catalyst (wt ratio) | CO Conversion (%) | Composition of Hydrocarbon Products (wt %) | | | |
|---|---|---|---|---|---|---|
| | | | CH$_4$ | C$_2$-C$_4$ | C$_5$-C$_{10}$ Aliphatic Hydrocarbons | Aromatic Hydrocarbons |
| S-24 | Fe$_2$O$_3$—TiO$_2$—ZnO—K$_2$O (100:100:10:3) | 92 | 25 | 27 | 28 | 20 |
| S-25 | Fe$_2$O$_3$—V$_2$O$_5$—ZnO—K$_2$O (100:100:10:5) | 94 | 27 | 28 | 25 | 20 |
| S-26 | Fe$_2$O$_3$—CuO—ZnO—K$_2$O (100:100:10:5) | 91 | 24 | 25 | 29 | 22 |
| S-27 | Fe$_2$O$_3$—MnO (100:100) | 93 | 26 | 30 | 20 | 24 |
| S-28 | CoO—ThO$_2$—MgO—kieselguhr (100:5:8:100) | 97 | 33 | 29 | 22 | 16 |
| S-29 | Fe$_2$O$_3$—CuO—K$_2$O—kieselguhr (100:10:4:100) | 95 | 25 | 28 | 27 | 20 |

Table 13-continued

| Catalyst No. | CO Reducing Catalyst (wt ratio) | CO Conversion (%) | Composition of Hydrocarbon Products (wt %) | | | |
|---|---|---|---|---|---|---|
| | | | $CH_4$ | $C_2-C_4$ | $C_5-C_{10}$ Aliphatic Hydrocarbons | Aromatic Hydrocarbons |
| S-30 | $Ru/Al_2O_3$ (0.5:100) | 89 | 28 | 15 | 57 | 0 |

EXAMPLE 14

Crystalline Silicate 1 synthesized in Example 1 was subjected to ion exchange with 0.1% by weight of ruthenium to obtain Catalyst S-31 and on the other hand, it was subjected to supporting of 1.0% by weight of ruthenium to obtain Catalyst S-32.

These catalysts were respectively contacted with a mixed gas of hydrogen and carbon monoxide ($H_2/CO=2$) under conditions of a pressure of 40 Kg/cm$^2$ abs., a temperature 300° C. and a GHSV of 1000 h$^{-1}$ to obtain results as shown in Table 14:

| Catalyst No. | Catalyst Making Treatment | Conversion | $CH_4$ | $C_2-C_4$ | Aliphatic Hydrocarbons | Aromatic Hydrocarbons |
|---|---|---|---|---|---|---|
| 31 | Ion Exchange with 0.1 wt % of Ru | 53 | 14 | 27 | 39 | 20 |
| 32 | Impregnating of 1.0 wt % of Ru | 80 | 21 | 26 | 34 | 19 |

EXAMPLE 15

A mixture of Crystalline Silicate 1 synthesized in Example 1 and ferric oxide in the same proportion by weight was subjected to supporting of 0.5% by weight of ruthenium, rhodium, platinum or palladium to prepare Catalysts S-33 to S-36.

These catalysts were respectively contacted with a mixed gas of hydrogen and carbon monoxide ($H_2/CO=2$) under conditions of a pressure of 20 Kg/cm$^2$, a temperature of 300° C. and a GHSV of 1000 h$^{-1}$ to obtain results as shown in Table 15:

TABLE 15

| Catalyst No. | Metal supported on Mixture of Crystalline Silicate and Iron Oxide | CO Conversion % | Composition of Hydrocarbon Products (wt %) | | | |
|---|---|---|---|---|---|---|
| | | | $CH_4$ | $C_2-C_4$ | $C_5-C_{10}$ Aliphatic Hydrocarbons | Aromatic Hydrocarbons |
| S-33 | Ruthenium | 89 | 24 | 26 | 35 | 15 |
| S-34 | Rhodium | 83 | 12 | 22 | 36 | 30 |
| S-35 | Platinum | 86 | 26 | 26 | 34 | 14 |
| S-36 | Palladium | 71 | 24 | 30 | 32 | 14 |

COMPARATIVE EXAMPLE 2

In the catalytic reactions of a mixed gas of hydrogen and carbon monoxide in Examples 11 to 13, the methanol synthesis catalysts or Fischer-Tropsch catalysts alone without Crystalline Silicates were respectively contacted with a mixed gas of hydrogen and carbon monoxide under conditions as shown in Table 16 to obtain results as shown in Table 16:

TABLE 16

| Catalyst | Pressure (Kg/cm$^2$ abs) | Temperature (°C.) | Reaction Products |
|---|---|---|---|
| Methanol Synthesis Catalyst (Reaction of Example 11) | 40 | 400 | Main Components: Methanol and $CH_4$ ($C_2-C_4/C_1 = \frac{1}{4}$) |
| Eischer-Tropsch Synthesis Catalyst (Reaction of Example 12) | 20 | 350 | $CH_4$: 40 wt %, $C_2-C_4$: 45 wt % $C_5-C_{10}$: 15 wt % (free of Aromatics) |
| $Re_2O_3$—$TiO_2$—$ZnO$—$K_2O$ (100:100:10:5) (Reaction of Example 13) | 10 | 300 | $CH_4$: 12 wt %, $C_2-C_4$: 62 wt % $C_5-C_{10}$: 26 wt % (free of Aromatics) |
| $Fe_2O_3$—$CuO$—$K_2O$—diatom earth (100:10:4:100) (Reaction of Example 13) | 20 | 230 | $CH_4$: 5 wt %, $C_2-C_4$: 13 wt % $C_5-C_{12}$: 22 wt %, $C_{13+}$: 56 wt % Oxygen-containing Compounds: 4 wt % |
| $Ru/Al_2O_3$ (0.5:100) (Raaction of Example 13) | 40 | 300 | $C_1-C_4$: 100 wt % |

As evident from Table 16, in the case of using the carbon monoxide reducing catalysts without Crystalline Silicates, there were obtained no products which can be used as gasoline as such.

It will clearly be understood from the foregoing Examples that the crystalline silicates of the present invention are useful as catalysts having each a much higher activity as well as higher selectivity for various conversion reactions, for example, conversion reactions of organic compounds such as synthesis of hydrocarbons from alcohols and/or ethers, and synthesis reactions of hydrocarbons from the synthesis gases. In addition, lower olefins can be obtained with a higher selectivity by controlling the reaction conditions, for example, by shortening the contacting or reaction time.

Since the crystalline silicates of the present invention have a uniform and small pore diameter, e.g. 5 to 7 Å and a capacity of adsorbing organic compounds but hardly adsorbing water, they can also be used as an adsorbent for separation of mixed solutions or mixed gases utilizing their characteristic properties.

What is claimed is:

1. A process for the production of hydrocarbons, which comprises contacting the synthesis gas with a mixed catalyst of (a) a crystalline silicate having a chemical composition represented by the following formula in terms of mole ratios of oxides under a dehydrated state:

$$(0.1-2) R_{2/n}O \cdot [aLa_2O_2 \cdot bCe_2O_3 \cdot ySiO_2]$$

in which R is at least one of mono- and divalent cations, n is the valence of R and $a+b=1$, $a \geqq 0$, $b \geqq 0$ and $y \geqq 12$, and (b) a carbon monoxide reducing catalyst at a temperature of 200° to 500° C. under a pressure of at most 300 atm.

2. The process of claim 1, wherein the carbon monoxide reducing catalyst consists of at least one metal selected from the group consisting of Group IB, IIB, IIIB, IVB, VB, VIB, VIIB and VIII elements of Periodic Table, and mixtures thereof, and oxides thereof.

3. The process of claim 2, wherein the carbon monoxide reducing catalyst consists of at least one combinations of chromium oxide and metallic zinc or metallic copper, chromium oxide and zinc oxide or copper oxide, alumina and metallic zinc or metallic copper and alumina and zinc oxide or copper oxide.

4. The process of claim 1, wherein the carbon monoxide reducing catalyst to crystalline silicate ratio is 0.1:100 to 100:1.

5. The process of claim 2, wherein the carbon monoxide reducing catalyst to crystalline silicate ratio is 0.1:100 to 100:1.

6. The process of claim 3, wherein the carbon monoxide reducing catalyst to crystalline silicate ratio is 0.1:100 to 100:1.

* * * * *